US010052297B2

(12) United States Patent
Dechelette et al.

(10) Patent No.: US 10,052,297 B2
(45) Date of Patent: Aug. 21, 2018

(54) L-SERINE TO BE USED AS A DRUG FOR PREVENTING AND/OR TREATING AN INFLAMMATORY RESPONSE OF THE SKIN

(75) Inventors: Corinne Dechelette, Rabastens (FR); Nathalie Castex Rizzi, Colomiers (FR); Laetitia Bonzom, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 13/381,583

(22) PCT Filed: Jul. 1, 2010

(86) PCT No.: PCT/EP2010/059401
§ 371 (c)(1),
(2), (4) Date: Mar. 16, 2012

(87) PCT Pub. No.: WO2011/000930
PCT Pub. Date: Jan. 6, 2011

(65) Prior Publication Data
US 2012/0172446 A1    Jul. 5, 2012

(30) Foreign Application Priority Data

Jul. 1, 2009  (FR) .................................. 09 54497

(51) Int. Cl.
| | | |
|---|---|---|
| *A61K 31/198* | (2006.01) | |
| *A61P 17/00* | (2006.01) | |
| *A61P 17/04* | (2006.01) | |
| *A61P 17/08* | (2006.01) | |
| *A61P 29/00* | (2006.01) | |
| *A61P 17/06* | (2006.01) | |
| *A61K 8/34* | (2006.01) | |
| *A61K 8/44* | (2006.01) | |
| *A61K 8/96* | (2006.01) | |
| *A61K 33/00* | (2006.01) | |
| *A61Q 19/00* | (2006.01) | |

(52) U.S. Cl.
CPC ............ *A61K 31/198* (2013.01); *A61K 8/345* (2013.01); *A61K 8/44* (2013.01); *A61K 8/965* (2013.01); *A61K 33/00* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,425,954 A | 6/1995 | Thompson et al. | |
| 5,472,698 A * | 12/1995 | Rawlings ................ | A61K 8/44 424/401 |
| 2003/0008018 A1 | 1/2003 | Miller et al. | |
| 2010/0035816 A1* | 2/2010 | Piccirilli ............. | A61K 31/198 514/2.5 |
| 2011/0098229 A1* | 4/2011 | Paul ........................... | 514/18.6 |

FOREIGN PATENT DOCUMENTS

| | | |
|---|---|---|
| EP | 1 762 241 A1 | 3/2007 |
| EP | 1 844 784 A1 | 10/2007 |
| JP | 8-217695 A | 8/1996 |
| JP | 11-60435 A | 3/1999 |
| JP | 11-209285 A | 8/1999 |
| JP | 2001-278796 A | 10/2001 |
| JP | 2002-316929 A | 10/2002 |
| JP | 2003-89658 A | 3/2003 |
| JP | 2005-40403 A | 2/2005 |
| JP | 2007-84460 A | 4/2007 |
| WO | WO 00/52051 A1 | 9/2000 |
| WO | WO 2005/063266 A1 | 7/2005 |
| WO | WO 2005/074910 A1 | 8/2005 |
| WO | WO 2009/084200 A1 | 7/2009 |

OTHER PUBLICATIONS

Miyamoto, Itch-Associated Response Induced by Experimental Dry Skin in Mice, Jpn. J. Pharmacol., 2002, 88, pp. 285-292.*
Hachem et al, "Serine Protease Signaling of Epidermal Permeability Barrier Homeostasis", Journal of Investigative Dermatology, vol. 126, 2006, pp. 2074-2086.
Hou et al., "Immunolocalization of Protease-Activated Receptor-2 in Skin: Receptor Activation Stimulates Interleukin-8 Secretion by Keratinocytes in vitro", Immunology, vol. 94, 1998, pp. 356-362.
Rattenholl et al., "Proteinase-Activated Receptor-2 in the Skin: Receptor Expression, Activation and Function During Health and Disease", Drug News Perspect, vol. 21, No. 7, Sep. 2008, pp. 369-381.
Seiberg et al., "The Protease-Activated Receptor 2 Regulates Pigmentation via Keratinocyte-Melanocyte Interactions", Experimental Cell Research, vol. 254, 2000, pp. 25-32.
Steinhoff et al., "Proteinase-Activated Receptor-2 in Human Skin: Tissue Distribution and Activation of Keratinocytes by Mast Cell Tryptase", Experimental Dermatology, vol. 8, 1999, pp. 282-294.
Steinhoff et al., "Proteinase-Activated Receptor-2 Mediates Itch: A Novel Pathway for Pruritus in Human Skin", The Journal of Neuroscience, vol. 23, No. 15, Jul. 16, 2003, pp. 6176-6180.
International Search Report for PCT/EP2010/059401 dated Sep. 3, 2010.

(Continued)

*Primary Examiner* — Kathrien Ann Cruz
*Assistant Examiner* — Andrew P Lee
(74) *Attorney, Agent, or Firm* — Birch, Stewart, Kolasch & Birch, LLP

(57) ABSTRACT

The invention relates to the use of L-serine as a drug for preventing and/or treating an inflammatory response of the skin caused by the overexpression and/or the overactivation of PAR2 receptors.

7 Claims, No Drawings

(56) References Cited

OTHER PUBLICATIONS

Japanese Office Action, dated Apr. 22, 2016, for Japanese Application No. 2012-518093, along with an English translation.
Korean Office Action, dated Jun. 27, 2016, for Korean Application No. 10-2012-7002254, along with an English translation.

* cited by examiner

L-SERINE TO BE USED AS A DRUG FOR PREVENTING AND/OR TREATING AN INFLAMMATORY RESPONSE OF THE SKIN

The present invention relates to the use of L-serine as a drug for preventing and/or treating an inflammatory response of the skin caused by overexpression/overactivation of PAR2 receptors, as well as in particular to a dermocosmetic composition comprising L-serine, Avène thermal spring water, glycerin and a cosmetically-acceptable carrier.

Protease-activated receptor-2 (PAR2) is associated with the physiopathology of several diseases involving inflammatory responses (Rattenholl A et al.; Drug News Perspect; 2008 September;21(7):369-81).

PAR2 belongs to the superfamily of 7-transmembrane receptors coupled to G proteins, but has a unique activation pathway. Indeed, PAR2 is activated by serine proteases such as trypsin, tryptase and factors Xa and VIIa. Cleavage by these proteases of the extracellular portion of the receptor exposes a new amino-terminal domain (SLIGKV) which acts as a ligand "attached" to the receptor: it binds upon itself at extracellular loop 2 and undergoes autoactivation.

PAR2 is expressed by the various cell types of the skin: keratinocytes, myoepithelial cells of the sweat glands, hair follicles, dendritic-like cells of the dermis and endothelial cells of the lamina propria and of the dermis (Steinhoff et al., Exp Dermatol.; 1999 August;8(4):282-94).

Melanocytes do not express this receptor although PAR2 plays an important role in pigmentation by promoting the transfer of melanin from melanocytes to keratinocytes (Seiberg et al., Exp Cell Res.; 2000 Jan. 10;254(1):25-32). Serine proteases generated by the epidermis have chemotactic effects that induce leucocyte recruitment in the skin. They are also involved in the regulation of homeostasis, mitogenesis and epidermal differentiation and they modulate the barrier function of the skin. Moreover, serine proteases contribute to the physiopathology of cutaneous diseases related to inflammation, host defense, carcinogenesis, fibrosis and nerve stimulation.

The physiological and physiopathological cutaneous properties of serine proteases are in part related to PARs. Indeed, PAR2 are overexpressed in the epidermis, dermis and vessels in inflammatory diseases of the skin such as atopic dermatitis, lichen planus and psoriasis (Steinhoff et al., Exp Dermatol; 1999 August;8(4):282-94).

PAR2 also play a role in the development of pruritus in patients suffering from atopic dermatitis (Steinhoff et al., J Neurosci. 2003 Jul. 16;23(15):6176-80).

Activation of PAR2 by a trypsin-type protease induces the production of IL-8 from keratinocytes (HaCaT) (Hou et al., Immunology, 1998, 94:356-362). In subjects with sensitive skin, it has been shown that PAR2 are overactivated. A consequence of the overactivation of PAR2 in sensitive nerve fibers is a sensation of cutaneous discomfort. Moreover, a consequence of the overactivation of PAR2 in keratinocytes is inflammation and restoration of the slowed barrier function (slowed secretion of lamellar bodies) (Hachem J P et al., J Invest Dermatol.; 2006 September;126 (9):2074-86.).

There is thus a genuine need to develop active agents that decrease PAR2 expression and/or activity.

In a surprising manner, the Applicant has demonstrated that L-serine, L-asparagine and/or L-valine each enable inhibition of PAR2 expression/activation.

Thus, the present invention relates to L-serine and/or L-asparagine and/or L-valine for use as a drug for preventing and/or treating an inflammatory response of the skin caused by overexpression and/or overactivation of PAR2.

Advantageously, the present invention relates to L-serine for use as a drug for preventing and/or treating an inflammatory response of the skin caused by overexpression and/or overactivation of PAR2.

Advantageously, the inflammatory response of the skin caused by overexpression and/or overactivation of PAR2 is responsible for an inflammatory pathology of the skin selected from the group consisting of atopic dermatitis, lichen planus, psoriasis, pruritus, seborrheic dermatitis, rosacea, couperosis and cutaneous hypersensitivity.

Thus, advantageously, the present invention relates to L-serine and/or L-asparagine and/or L-valine for use as a drug for preventing and/or treating an inflammatory pathology of the skin selected from the group consisting of atopic dermatitis, lichen planus, psoriasis, pruritus, seborrheic dermatitis, rosacea, couperosis and cutaneous hypersensitivity.

L-serine is a C3 α-amino acid, a hydroxylated homologue of alanine.

L-serine is a hydroxylated aliphatic amino acid whose systematic name is 2-amino-3-hydroxypropanoic acid with the following formula:

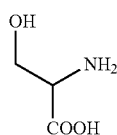

L-asparagine (or asparagine-amino-succinic acid) is an uncharged and hydrophilic polar α-amino acid, derived from aspartic acid, with the following formula:

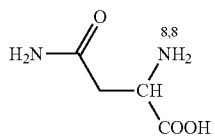

L-valine is a nonpolar and hydrophobic α-amino acid with the following formula:

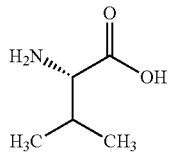

"Overexpression of PAR2" means that said receptors are expressed in greater number than under normal physiological conditions.

"Overactivation of PAR2" means that said receptors exhibit greater activity than when under normal physiological conditions.

Thus, L-serine and/or L-asparagine and/or L-valine are used to inhibit PAR2.

To "inhibit PAR2" means to inhibit and/or to decrease PAR2 expression, as well as to inhibit and/or to decrease PAR2 activity.

In the context of the present invention, the terms "to prevent" and "prevention" mean to avoid the appearance of a disease, a disorder or one or more signs and/or symptoms.

Advantageously, L-serine and/or L-asparagine and/or L-valine are used in combination with Avène thermal spring water.

In a preferred manner, L-serine is used in combination with Avène thermal spring water.

The composition of Avène thermal spring water is as follows:

| Composition in mg/l | Avène |
|---|---|
| Chlorides | 5.4 |
| Bicarbonates | 226.7 |
| Hydrogen carbonates | |
| Sulfates | 13.1 |
| Silicates | |
| Silica | 14 |
| Nitrates | |
| Calcium | 42.7 |
| Magnesium | 21.2 |
| Sodium | 4.8 |
| Potassium | 0.8 |
| Iron | 0.005 |
| Selenium | 0.005 |
| Silicon | |
| Zinc | 0.02 |
| Copper | 0.005 |
| Dry residue | 207 |
| Mineral content | Low |
| pH | 7.5 |
| Osmolarity | Hypotonic |

Advantageously, L-serine and/or L-asparagine and/or L-valine are used in combination with glycerin.

In a preferred manner, L-serine is used in combination with glycerin.

Still more advantageously, L-serine and/or L-asparagine and/or L-valine are used in combination with Avène thermal spring water and glycerin.

In a preferred manner, L-serine is used in combination with Avène thermal spring water and glycerin.

Glycerin or glycerol refers to a propane-1,2,3-triol of the following formula:

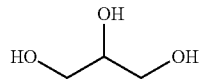

Preferably, L-serine and/or L-asparagine and/or L-valine will be used at a concentration greater than 30 µM, preferably at a concentration greater than 50 µM, more preferably greater than 80 µM, and in a particularly preferred manner greater than 100 µM.

According to another aspect, the present invention relates to a pharmaceutical composition comprising L-serine and/or L-asparagine and/or L-valine to be used as a drug for preventing and/or treating an inflammatory response of the skin caused by overexpression and/or overactivation of PAR2.

In a preferred manner, the present invention relates to a pharmaceutical composition comprising L-serine for use as a drug for preventing and/or treating an inflammatory response of the skin caused by overexpression and/or overactivation of PAR2.

Preferably, said composition is a dermatological composition.

In a particularly preferred manner, said composition is for topical application.

"Topical application" refers to application directly on the skin.

Advantageously, the pharmaceutical composition further comprises Avène thermal spring water and/or glycerin, preferably to the exclusion of any other active agent exhibiting an inflammatory effect, and in a particularly preferred manner to the exclusion of any other active agent.

In another embodiment of the present invention, L-serine and/or L-asparagine and/or L-valine are the only active agents of the composition exhibiting an anti-inflammatory effect, and in a particularly preferred manner are the only active agents.

In a preferred manner, L-serine is the only active agent of the composition exhibiting an anti-inflammatory effect, and in a particularly preferred manner is the only active agent.

In a particular embodiment according to the invention, the composition according to the present invention may further comprise active agents intended in particular for the prevention and/or the treatment of cutaneous affections.

Preferably, the composition according to the present invention is used as a drug for preventing and/or treating sensitive skin.

Generally, sensitive skins are defined by a particular reactivity of the skin.

This cutaneous reactivity is typically expressed by the manifestation of signs of discomfort in response to bringing the subject in contact with a triggering element which may have diverse origins. It may be a question of applying a cosmetic product on the surface of the sensitive skin, eating certain foods, exposure to sudden variations of temperature, air pollution and/or ultraviolet or infrared radiation. There are also associated factors such as age and skin type. For example, sensitive skins are more frequent among those with dry or oily skins compared to those with normal skin. In the context of the present invention, sensitive skin encompasses irritable skin and intolerant skin.

Intolerant skin is skin that reacts by heating, tightness or tingling sensations and/or redness to various factors such as the application of cosmetic or dermatological products or of soap. In general, these signs are associated with erythema and with hyperseborrheic or acneic, or even rosaceiform, skin, with or without dry patches.

Irritable skin is skin that reacts by pruritus, that is to say by itching or by stinging, to various factors such as the environment, the emotions, food, the wind, friction, shaving, hard water with a high calcium concentration, temperature variations, moisture, etc.

Advantageously, the inflammatory response of the skin caused by overexpression and/or overactivation of PAR2 receptors is responsible for an inflammatory pathology of the skin, wherein said pathology is preferably selected from the group consisting of atopic dermatitis, lichen planus, psoriasis, pruritus, seborrheic dermatitis, rosacea, couperosis and cutaneous hypersensitivity.

Thus, advantageously, the present invention relates to a pharmaceutical composition comprising L-serine and/or L-asparagine and/or L-valine for use as a drug for preventing and/or treating a pathology selected from the group comprising atopic dermatitis, lichen planus, psoriasis, pruritus, seborrheic dermatitis, rosacea, couperosis and cutaneous hypersensitivity.

Atopic dermatitis is described as associated with a deficit in the metabolism of lipids of the stratum corneum and in particular of ceramides. This pathology is expressed in the form of a more or less chronic xerosis extending over a large portion of the body, associated with inflammatory and pruriginous eruptions in patches.

Psoriasis is also a cutaneous inflammatory disease of chronic progression which affects 2% of the population. It is characterized by abnormal growth of epidermal cells associated with an inflammatory response.

Lichen planus, which has a random appearance, is an autoimmune disease likely related to stress. It begins suddenly, similar to an allergy: the skin becomes covered with eczematous-squamous papules, causing itching. Lichen planus may be generalized or confined to small areas of the skin. Muscle or rheumatic pain may accompany eruptions of lichen planus. The disease may last for 12 to 15 months.

Seborrheic dermatitis is a dermatosis of the face and scalp, characterized by red patches with indistinct contours, with thin nonadherent squamae.

Rosacea is an initially benign, incurable cutaneous disease which appears as chronic redness on the nose and cheeks and sometimes on the chin and forehead. These symptoms are accompanied by a tingling sensation, in particular around the eyes.

Couperosis is a state of permanent redness of the convex areas of the face (nose, cheeks, forehead, chin . . . ), sometimes with small vessels visible to the naked eye.

Preferably, the composition according to the present invention will comprise between 0.01% and 10% by weight of L-serine and/or L-asparagine and/or L-valine in relation to the total weight of the composition and preferably between 0.5% and 3% of L-serine and/or L-asparagine and/or L-valine in relation to the total weight of the composition.

In a preferred manner, the composition according to the present invention will comprise between 0.01% and 10% by weight of L-serine in relation to the total weight of the composition and preferably between 0.5% and 3% of L-serine in relation to the total weight of the composition.

The composition according to the invention may be formulated to be administered by topical, oral, subcutaneous, injectable, rectal or genital route.

Preferably, the composition according to the invention is formulated to be administered by topical route.

The compositions according to the invention may be provided in all galenic forms normally used according to the mode of administration desired.

The carrier may be of various natures according to the type of composition desired.

More particularly, with regard to compositions intended for administration by topical route, the carrier may be aqueous, hydroalcoholic or oil solutions, dispersions in solution form or dispersions in lotion or serum form, liquid emulsions or milky semi-fluid emulsions, creamy suspensions or emulsions, aqueous or anhydrous gels, microemulsions, microcapsules, microparticles or ionic and/or nonionic vesicular dispersions. These compositions are prepared according to standard methods.

These compositions may in particular constitute creams for cleansing, protecting, treating or caring for the face, hands, feet, large anatomical folds or the body (for example day creams, night creams, make-up removal creams, foundation creams, sunblock creams), make-up products such as fluid foundations, make-up removal milks, milks for body protection or care, after-sun milks, skin care lotions, gels or foams, such as cleansing or disinfection lotions, sunblock lotions, artificial tanning lotions, compositions for the bath, deodorant compositions containing a bactericidal agent, after-shave gels or lotions, depilatory creams, or compositions to prevent insect bites.

The compositions according to the invention may also consist of solid preparations constituting soaps or cleansing bars.

They may be also used for the hair in the form of solutions, creams, gels, emulsions, foams or in the form of aerosol compositions containing a pressurized propellant.

When the composition of the invention is an emulsion, the proportion of the fatty phase may range from 5% to 80% by weight, and preferably from 5% to 50% by weight in relation to the total weight of the composition. The oils, emulsifiers and co-emulsifiers used in the composition in emulsion form are selected from those typically used in the cosmetics and/or dermatological field.

The emulsifier and co-emulsifier may be present in the composition in a proportion ranging from 0.3% to 30% by weight, and preferably from 0.5% to 15% by weight in relation to the total weight of the composition.

When the composition of the invention is an oily gel, the fatty phase may represent more than 90% of the total weight of the composition.

The cosmetic and/or dermatological composition of the invention may also contain adjuvants typically used in the cosmetics, pharmaceutical and/or dermatological field, such as hydrophilic or lipophilic gelling agents, hydrophilic or lipophilic active agents, preservatives, antioxidants, solvents, fragrances, loads, filters, bactericides, odor absorbers and colorants. The quantities of these various adjuvants are those typically used in the field in question, for example from 0.01% to 35% of the total weight of the composition.

These adjuvants, according to their nature, may be introduced into the fatty phase and/or the aqueous phase.

As fats that may be used in the invention, mention may be made of mineral oils such as, for example, hydrogenated polyisobutene and petroleum oil, vegetable oils such as, for example, a liquid fraction of shea butter, sunflower and apricot kernel oil, animal oils such as, for example, perhydrosqualene, synthetic oils, notably PurCellin oil, isopropyl myristate and ethylhexyl palmitate, and fluorinated oils such as, for example, perfluoropolyethers. Fatty alcohols, fatty acids such as, for example, stearic acid and such as, for example, waxes, notably paraffin, carnauba and beeswax may also be used. Silicone compounds such as silicone oils and, for example, cyclomethicone and dimethicone, waxes, resins and silicone gums may also be used.

As emulsifiers that may be used in the invention, mention may be made of, for example, glycerol stearate, polysorbate 60, the mixture of cetyl-stearyl alcohol and cetyl-stearyl alcohol oxyethylenated with 33 moles of ethylene oxide sold under the name Sinnowax AO® by HENKEL, the mixture of PEG-6/PEG-32/glycol stearate sold under the name Tefose® 63 by GATTEFOSSÉ, PPG-3 myristyl ether, silicone emulsifiers such as cetyl dimethicone copolyol and sorbitan mono- or tri-stearate, PEG-40 stearate and oxyethylenated sorbitan monostearate (20OE).

As solvents that may be used in the invention, mention may be made of lower alcohols, notably ethanol and isopropanol, and propylene glycol.

As hydrophilic gelling agents, mention may be made of carboxylic polymers such as carbomer, acrylic copolymers such as acrylate/alkyl acrylate copolymers, polyacrylamides, and in particular the mixture of polyacrylamide, C13-14-isoparaffin and laureth-7 sold under the name Sepigel 305® by SEPPIC, polysaccharides, for instance cellulose derivatives such as hydroxyalkylcelluloses, and in particular hydroxypropylcellulose and hydroxyethylcellulose, natural gums such as guar, carob and xanthan and clays.

As lipophilic gelling agents, mention may be made of modified clays such as bentones, fatty acid metal salts such as aluminum stearates and hydrophobic silica, or ethylcellulose and polyethylene.

Hydrophilic active agents that may be used include proteins or protein hydrolysates, amino acids, polyols, notably $C_2$ to $C_{10}$ polyols such as glycerol, sorbitol, butylene glycol and polyethylene glycol, urea, allantoin, sugars and sugar derivatives, water-soluble vitamins, starch, and bacterial or plant extracts such as those of aloe vera.

Lipophilic active agents that may be used include retinol (vitamin A) and derivatives of same, tocopherol (vitamin E) and derivatives of same, ceramides, essential oils and unsaponifiables (tocotrienol, sesame, gamma-oryzanol, phytosterols, squalenes, waxes, terpenes).

According to another aspect, the present invention relates to the cosmetic use of L-serine and/or L-asparagine and/or L-valine to inhibit PAR2.

In a preferred manner, the present invention relates to the cosmetic use of L-serine to inhibit PAR2.

According to another aspect, the present invention relates to a method of cosmetic and/or pharmaceutical treatment for preventing and/or treating an inflammatory response of the skin caused by overexpression and/or overactivation of PAR2, comprising at least one step of applying the pharmaceutical or cosmetic composition of the present invention.

The application step may, for example, be an application of creams, gels, serums, lotions, make-up removal milks or after-sun compositions on the skin or dry hair, application of a hair lotion on wet hair, shampoos, or application of toothpaste on the gums.

Preferably, said method is a dermatological method, comprising at least one step of applying on the skin a dermatological composition such as defined above.

The cosmetic and/or pharmaceutical method according to the invention may be implemented by topical application, every day for example, of the composition according to the invention.

The method according to the invention may comprise a single application step.

According to another embodiment, the cosmetic treatment method comprises the repetition of the application step two to three times per day for one day or more and generally for an extended period of at least four weeks, even four to 15 weeks, with one or more breaks as the case may be.

According to another aspect, the present invention relates to a composition comprising L-serine and/or L-asparagine and/or L-valine, Avène thermal spring water and glycerin, and a pharmaceutically or cosmetically acceptable carrier.

In a preferred manner, the present invention relates to a composition comprising L-serine, Avène thermal spring water and glycerin, and a pharmaceutically or cosmetically acceptable carrier.

Advantageously, said composition is a dermo-cosmetic composition.

Preferably, said composition includes no other active agent exhibiting an anti-inflammatory effect, and in a particularly preferred manner includes no other active agent.

EXAMPLE 1

HaCaT cell line keratinocyte models were used. L-serine and L-asparagine were purchased from EVONIK, L-arginine was purchased from AMINO and L-valine was purchased from AJINOMOTO.

A fluorescent probe (Fluo-4/AM at a concentration of 2 µM) is incorporated for 30 minutes in cells inoculated in 96-well plates and the active agent to be tested is incubated for 30 minutes. Only the deesterified form of the probe bound to calcium ions is excitable under 485 nm fluorescence and emits at 535 nm. The incubation buffer used is HBSS buffer supplemented with HEPES (20 mM) and with water-soluble probenecid (2.5 mM).

The cells were stimulated with 10 nM trypsin.

The reference molecule used is a STI molecule (soybean trypsin inhibitor) at a concentration of 1 µM.

L-serine and L-asparagine, solubilized at 50 mg/ml in distilled water (475.8 mM for L-serine and 378.4 mM for L-asparagine) were evaluated at concentrations of 3 µM, 10 µM, 30 µM and 100 µM.

L-arginine was solubilized at 100 mM in distilled water.

L-valine was solubilized at 200 mM in distilled water.

L-aspartic acid was solubilized at 200 mM in distilled water.

Calcium flow, which represents PAR2 activation, is measured by fluorescence, well by well in real time according to kinetics before and after the injection of trypsin. The percentage of inhibition of PAR2 activation corresponds to the percentage of inhibition of calcium flow.

The results presented in figure 1 show that the application of L-serine permitted to inhibit PAR2 activation in a dose-dependent manner.

The results presented in table 1 show that the application of L-asparagine permitted to inhibit PAR2 activation, but not in a dose-dependent manner.

The results presented in table 1 show that the application of L-valine permitted to inhibit PAR2 activation.

Moreover, the results show that L-arginine does not significantly inhibit PAR2 activation.

TABLE 1

| Percentage of inhibition | Anti-PAR2 activity (percentage of inhibition) | | | |
| --- | --- | --- | --- | --- |
| Concentration | 3 µM | 10 µM | 30 µM | 100 µM |
| L-serine | 3% | 13% | 20% | 33%*** |
| L-asparagine | 23%* | 23%* | 22%* | 31%*** |
| L-arginine | −17% | 12% | −11% | 1% |
| L-valine | 6% | 26%* | 20% | 34%*** |
| 1 µM STI | | 106-109%*** | | |

$p < 0.5$ and $p < 0.001$ (***) values significantly different than trypsin values (Dunnett's test)

EXAMPLE 2

The barrier function of the skin provides protection from the external environment. Epidermal keratinocytes may respond directly to a wide variety of irritants or allergens and participate actively in cutaneous processes involving inflammation and immunity, in particular through the synthesis and secretion of pro-inflammatory cytokines, mediators of protein origin.

The chemokine—interleukin-8 (IL-8)—which is expressed by keratinocytes and is heavily involved in amplification of the inflammatory response, has been studied in greater detail. The principal function of chemokines is to recruit and activate neutrophil granulocytes, notably by stimulating their secretion of pro-inflammatory molecules.

The test performed permitted to evaluate the anti-inflammatory activity of L-serine in terms of IL-8 secretion, stimulated by trypsin, on human keratinocytes from a cell line (HaCaT).

Principle of the IL-8 Assay: Sandwich ELISA for Quantification of IL-8 Secreted in Culture Supernatants.

IL-8 is captured by a monoclonal antibody bound to microplate wells. A second anti-IL-8 antibody is added. This antibody is biotinylated, which enabled the binding of streptavidin coupled with peroxidase activity. Adding the peroxidase substrate makes it possible to quantify the IL-8 concentration in each well by measuring absorbance at 450 nm.

Materials and Methods a) Cells:

The HaCaT human keratinocyte cell line was used.

b) Materials:

A 96-well microplate for cell culture and a plate reader with injectors, Mithras LB940TM (Berthold Technologies®), were used.

c) Reagents:

10 nM trypsin was used as stimulation agent.

Reagents from the Human CXCL8/IL8 DuoSet R&D System kit (ref. DY208(E)) were used.

d) Product Tested:

L-serine, solubilized at 475.8 mM in distilled water, was evaluated at concentrations of 3 µM, 10 µM, 30 µM, 100 µM, 300 µM and 1 mM.

e) Protocol:

L-serine is incubated for 1 hour at 37° C. (HBSS buffer). The stimulation agent (trypsin T03) is then added and incubated for 24 hours at 37° C.

The culture supernatants are recovered, centrifuged at +4° C. and then stored at −20° C.

The IL-8 concentrations of the samples are calculated from a standard curve of the following equation:

$$OD = (B_{max} * [IL\text{-}8])/(K_d + [IL\text{-}8])$$

Next, the percentages of inhibition of IL-8 secretion are calculated according to the following formula:

$$\% \text{ inhibition} = 100 - \left( \frac{Avg[IL\text{-}8](\text{Active agent}) - Avg[IL\text{-}8](\text{Control})}{Avg[IL\text{-}8](\text{Stimulation agent}) - Avg[IL\text{-}8](\text{Control})} * 100 \right)$$

Results

The values indicated in the table below represent L-serine inhibition of IL-8 secretion following trypsin stimulation of HaCaT keratinocytes.

Percentage of Inhibition of IL-8 Secretion:

Separate Experiments: (n=2)

TABLE 2

| Factor of induction of | % inhibition L-serine | | | |
|---|---|---|---|---|
| IL-8 by 10 nM trypsin | 10 µM | 30 µM | 100 µM | 1 mM |
| X 2.6 in relation to control cells (baseline production without stimulation) | 47* | 50* | 66* | 74* | p < 0.001 (***) values significantly different than trypsin values (Dunnett's test)

CONCLUSION

In vitro, on a cellular scale, pro-inflammatory stimulation such as PAR2 activation by trypsin induces IL-8 secretion by keratinocytes.

L-serine shows a significant inhibition of IL-8 secretion by keratinocytes following PAR2 stimulation by trypsin with an average inhibition of 74% at a concentration of 1 mM.

EXAMPLE 3

Composition According to the Invention

| INCI name | Percentage | Function |
|---|---|---|
| Water | QSP 100% | |
| Disodium EDTA | 0.2 | Complexing agent |
| Phenoxyethanol-Parabens | 0.8 | Preservative |
| Glycerin | 4 | Humectant |
| Carbomer | 0.5 | Gelling agent |
| Glyceryl stearate | 4 | Emulsifier, consistency factor |
| Cetearyl isononanoate | 3 | Emollient |
| Dimethicone | 5 | Emollient |
| Squalane | 5 | Emollient |
| Paraffinum Liquidum | 10 | Emollient |
| L-serine | 1 | Active agent |
| Triethanolamine | 0.30 | pH adjuster |

The invention claimed is:

1. Method for preventing and/or treating pruritus, said method comprising:
    topically administering L-serine to a patient in need thereof, wherein said method does not include preventing and/or treating psoriasis,
    wherein L-serine is the only anti-pruritus active agent.

2. Method for preventing and/or treating pruritus, said method comprising:
    topically administering a pharmaceutical composition comprising L-serine to a patient in need thereof, wherein said method does not include preventing and/or treating psoriasis,
    wherein L-serine is the only anti-pruritus active agent in the pharmaceutical composition.

3. Method according to claim 2, wherein said pharmaceutical composition further comprises thermal spring water.

4. Method according to claim 2, wherein said pharmaceutical composition further comprises glycerin.

5. Method for preventing and/or treating pruritus, said method comprising:
    topically administering a pharmaceutical composition comprising L-serine to a patient in need thereof, wherein said method does not include preventing and/or treating psoriasis,
    wherein L-serine is the only active agent of the composition.

6. Method according to claim 2, wherein the L-serine concentration is between 0.01% and 10% by weight in relation to the total weight of the composition.

7. Method according to claim 6, wherein the L-serine concentration is between 0.5% and 3% by weight in relation to the total weight of the composition.

* * * * *